(12) United States Patent
Cappellini

(10) Patent No.: US 11,911,252 B2
(45) Date of Patent: *Feb. 27, 2024

(54) ELASTIC FILM LAMINATE AND METHOD OF FORMING THE SAME

(71) Applicant: FIRST QUALITY PRODUCTS, INC., Great Neck, NY (US)

(72) Inventor: Pierluigi Cappellini, Bellefonte, PA (US)

(73) Assignee: First Quality Products, Inc., Great Neck, NY (US)

( * ) Notice: Subject to any disclaimer, the term of this patent is extended or adjusted under 35 U.S.C. 154(b) by 749 days.

This patent is subject to a terminal disclaimer.

(21) Appl. No.: 16/782,293

(22) Filed: Feb. 5, 2020

(65) Prior Publication Data

US 2020/0246202 A1 Aug. 6, 2020

Related U.S. Application Data

(63) Continuation of application No. 15/387,420, filed on Dec. 21, 2016, now Pat. No. 10,588,794.

(60) Provisional application No. 62/270,437, filed on Dec. 21, 2015.

(51) Int. Cl.
| | | |
|---|---|---|
| *A61F 13/15* | (2006.01) | |
| *A61F 13/62* | (2006.01) | |
| *A61F 13/56* | (2006.01) | |
| *B32B 27/12* | (2006.01) | |

(52) U.S. Cl.
CPC ........ *A61F 13/622* (2013.01); *A61F 13/5638* (2013.01); *B32B 27/12* (2013.01)

(58) Field of Classification Search
CPC ..... A61F 13/622; A61F 13/5638; B32B 27/12

USPC .................................................. 604/385.201
See application file for complete search history.

(56) References Cited

U.S. PATENT DOCUMENTS

| | | | | |
|---|---|---|---|---|
| 4,655,760 | A | * | 4/1987 | Morman ............... A61F 13/514 604/385.26 |
| 4,720,415 | A | * | 1/1988 | Vander Wielen ........................... A61F 13/15593 428/152 |
| 4,770,656 | A | | 9/1988 | Proxmire et al. |
| 10,588,794 | B2 | * | 3/2020 | Cappellini .............. B32B 27/12 |
| 2006/0099379 | A1 | | 5/2006 | Kling |
| 2007/0005038 | A1 | | 1/2007 | Mansfield et al. |
| 2008/0070464 | A1 | | 3/2008 | Alberg et al. |

FOREIGN PATENT DOCUMENTS

WO 94/14607 A1 7/1994

* cited by examiner

*Primary Examiner* — Jacqueline F Stephens
(74) *Attorney, Agent, or Firm* — Amster, Rothstein & Ebenstein LLP

(57) ABSTRACT

An elastic panel for use in an absorbent article including a first nonwoven web layer, a second nonwoven web layer and an elastomeric film layer disposed between the first and second nonwoven layers. At least one of the first and second nonwoven web layers includes at least one group of folded portions. Each folded portion includes a first fold line and a second fold line so that the folded portion is divided into a proximal section, a distal section and a medial section disposed between the proximal and distal sections. The proximal section is directly attached to the elastomeric film layer and the medial and distal sections are not directly attached to the elastomeric film layer so that the folded portions extend to allow the web panel to stretch elastically.

11 Claims, 13 Drawing Sheets

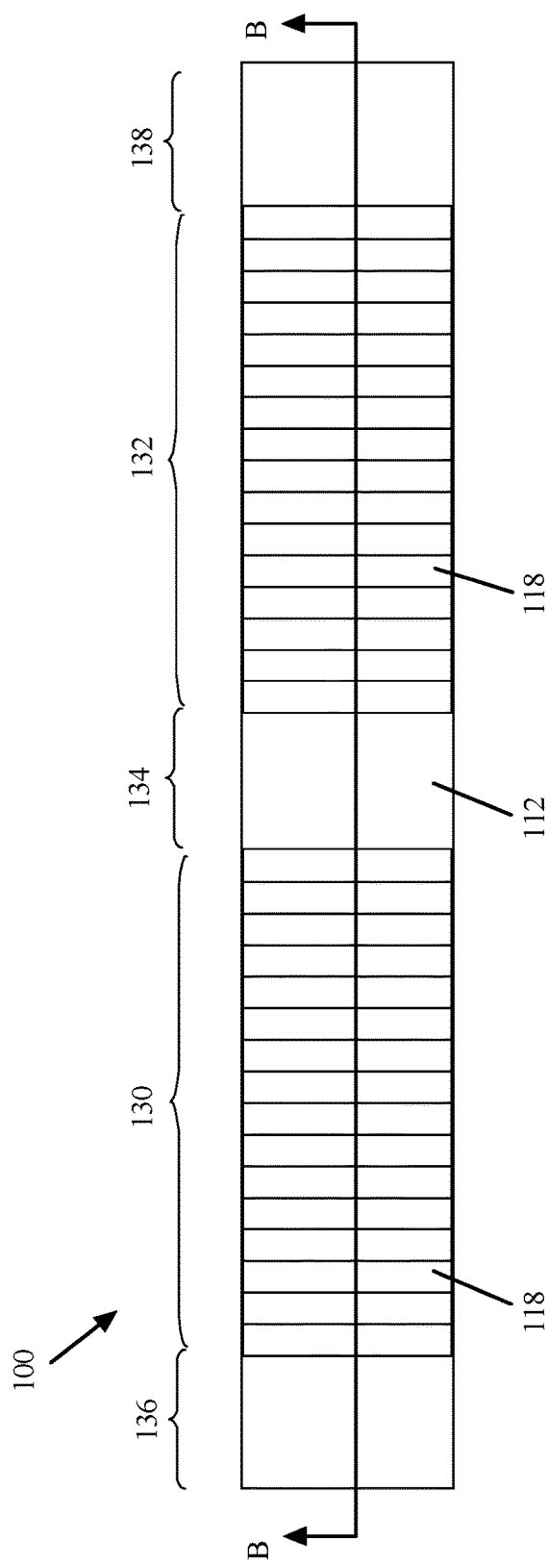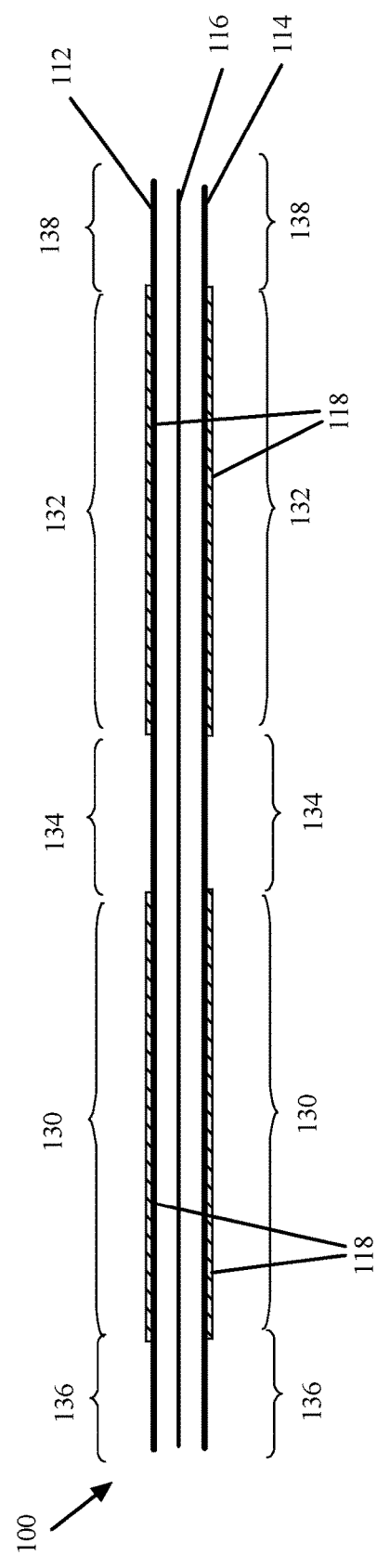
FIG. 3A
FIG. 3B

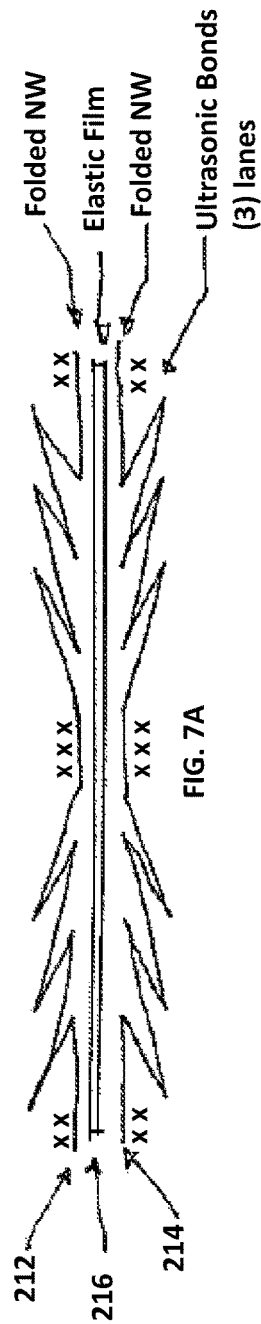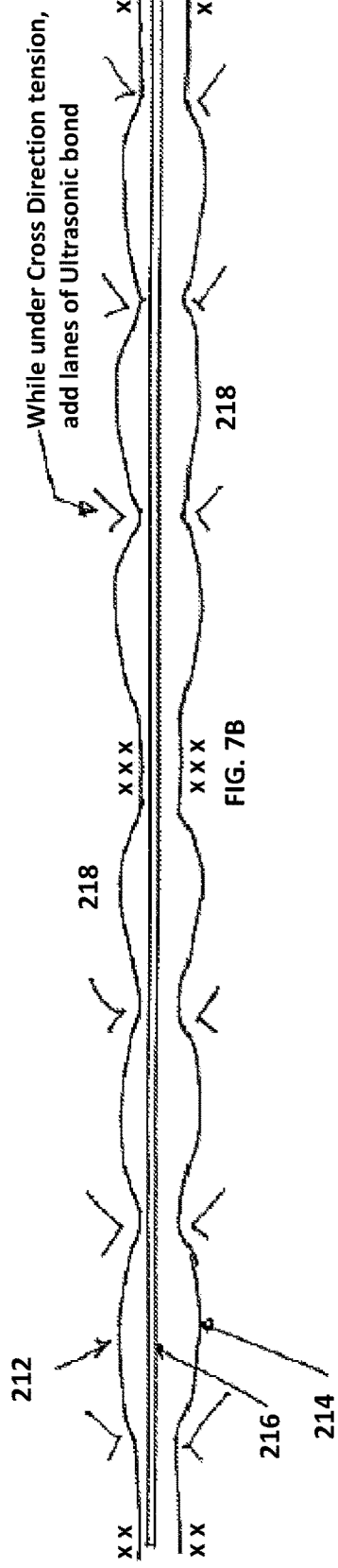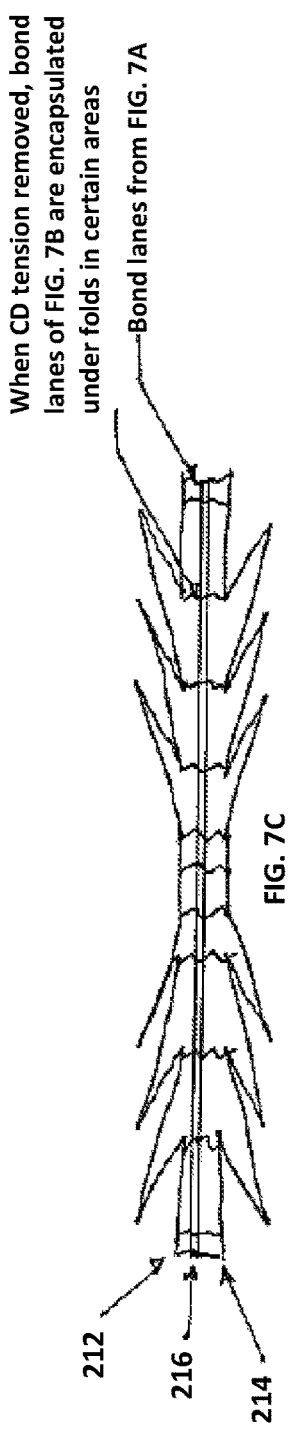

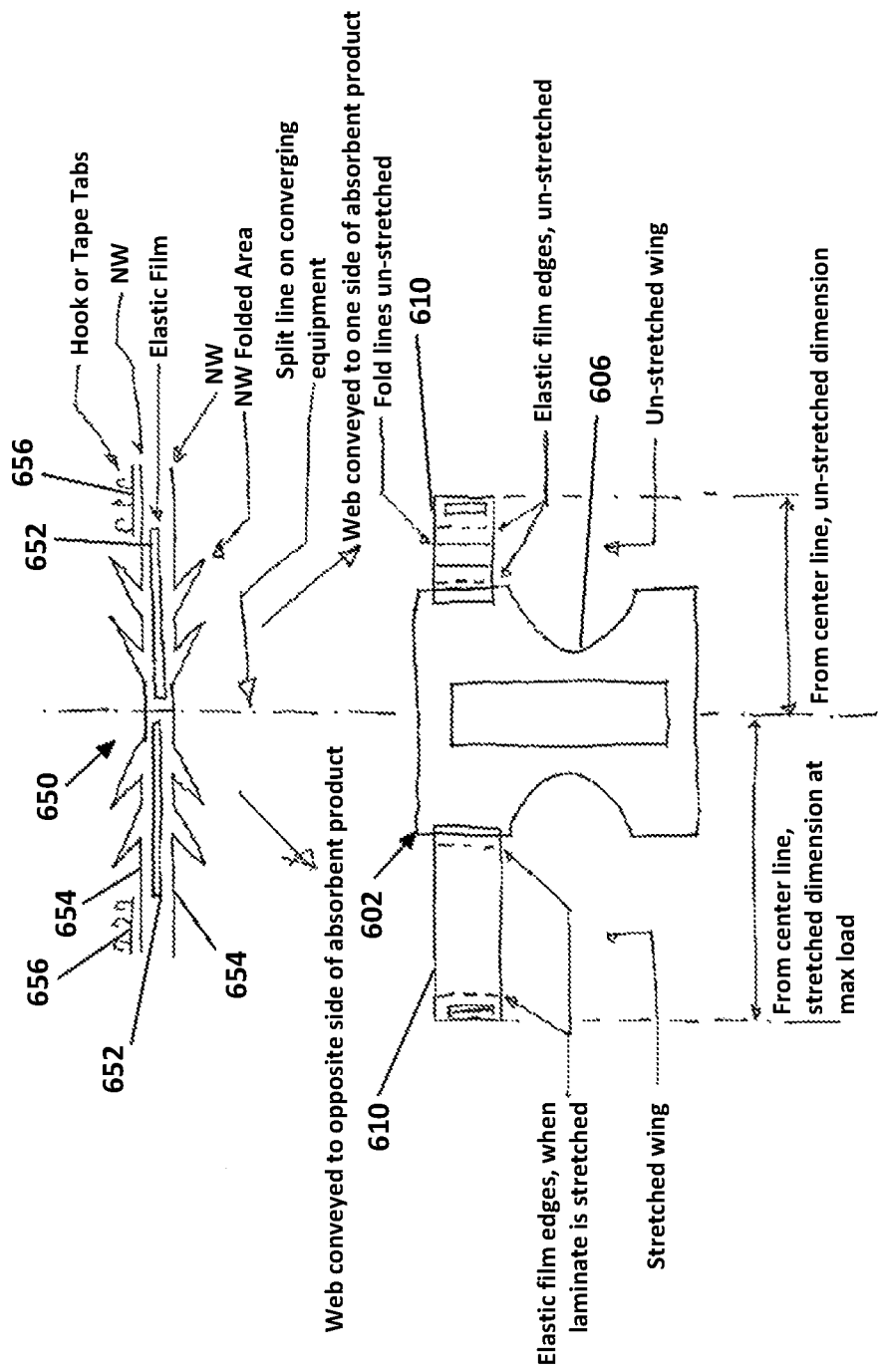

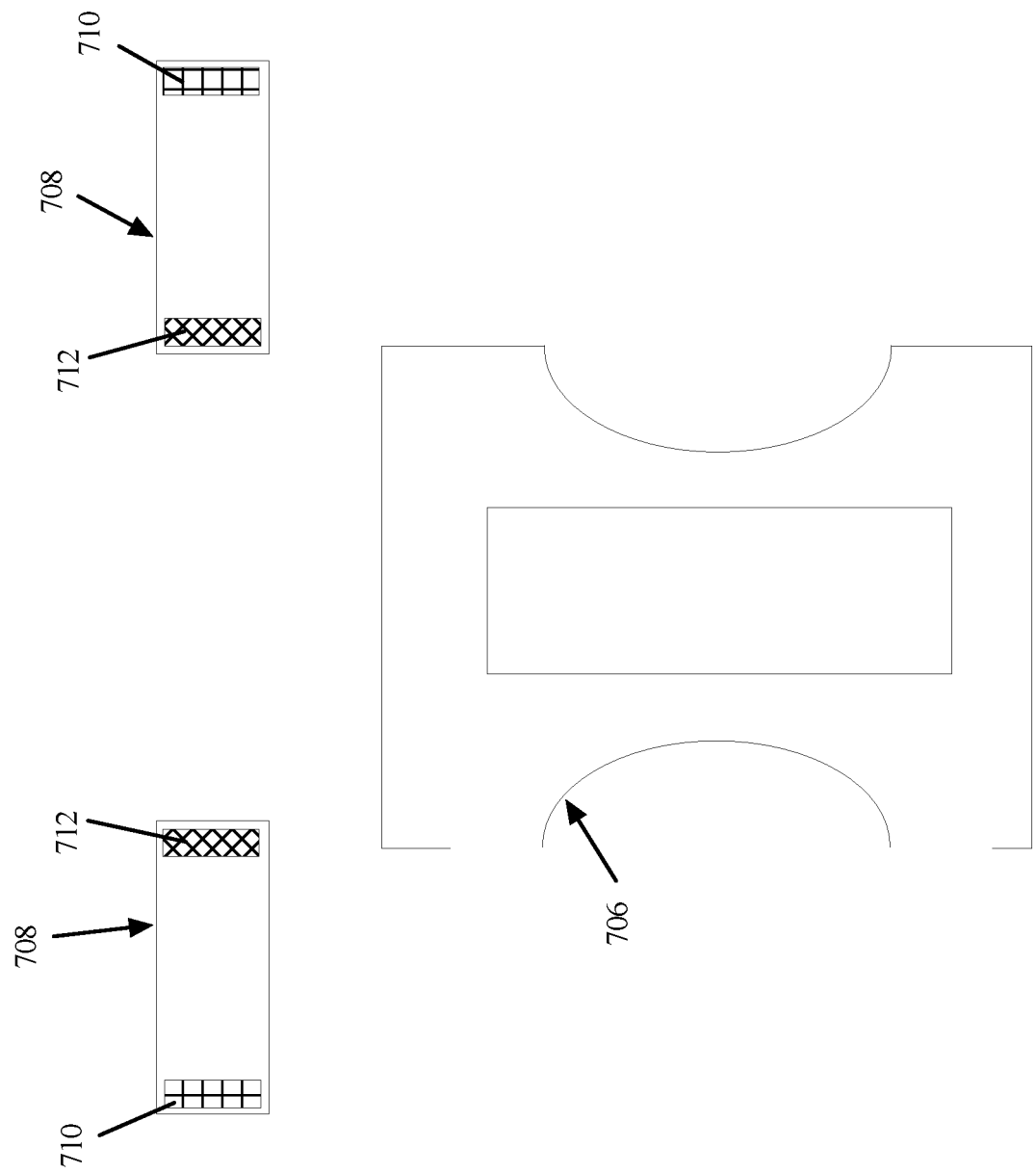

ELASTIC FILM LAMINATE AND METHOD OF FORMING THE SAME

RELATED APPLICATIONS

This application is a continuation of U.S. patent application Ser. No. 15/387,420, filed Dec. 21, 2016 and entitled ELASTIC FILM LAMINATE AND METHOD OF FORMING THE SAME, which in turn claims priority to U.S. Provisional Patent Application 62/270,437, filed Dec. 21, 2015 and entitled ELASTIC FILM LAMINATE AND METHOD OF FORMING THE SAME, the contents of which are incorporated herein by reference in their entirety.

FIELD

The present invention relates to elastic laminates, and more particularly, to elastic laminates that includes elastomeric films and nonwoven web layers.

BACKGROUND

Disposable absorbent articles are well known in the art. A non-exhaustive list of examples of absorbent articles includes diapers, diaper covers, disposable diapers, training pants, feminine hygiene products and adult incontinence products. Disposable absorbent articles typically include one or more components that exhibit elastic properties so that such components can be stretched around the wearer's anatomy for a closer fit. For example, the waist portion of a disposable article preferably has the ability to stretch so that the article can fit snugly against the wearer's waist.

It is known to construct certain components of absorbent articles with an elastomeric film so that the components exhibit elasticity. However, it is important to also provide such components with other characteristics to ensure the wearer's comfort, such as softness, breathability and dryness. Accordingly, some conventional elastic components are constructed as a laminate made of an elastomeric film and one or more layers of nonwoven material. An issue with such conventional laminates is that the non-elastic nonwoven layers tend to bunch up or pucker in an uneven manner at portions that are not directly fixed to the elastomeric film. This causes the overall diaper construction to take on a sloppy appearance and the uneven bunching of nonwoven material may cause discomfort to the wearer.

SUMMARY OF THE INVENTION

An object of the present invention is to provide an elastic laminate that includes nonwoven web layers that exhibit reduced bunching when the laminate is stretched as compared to conventional laminate constructions.

Another object of the present invention is to provide an elastic laminate that provides enhanced ventilation upon stretching as compared to conventional laminate constructions.

According to an exemplary embodiment of the present invention, an extendable and elastic panel for use in an absorbent article includes a first nonwoven web layer, a second nonwoven web layer and an elastomeric film layer disposed between the first and second nonwoven layers. At least one of the first and second nonwoven web layers includes at least one group of folded portions. Each folded portion includes a first fold line and a second fold line so that the folded portion is divided into a proximal section, a distal section and a medial section disposed between the proximal and distal sections. The proximal section is directly attached to the elastomeric film layer and the medial and distal sections are not directly attached to the elastomeric film layer so that the folded portions extend upon stretching of the elastomeric film layer.

In at least one embodiment, the at least one group of folded portions comprises a plurality of groups, and the at least one of the nonwoven web layers comprises generally planar sections between the plurality of groups.

In at least one embodiment, at least two of the proximal, medial and distal sections of the folded portions are bonded together.

In at least one embodiment, the at least two of the proximal, medial and distal sections of the folded portions are bonded together by ultrasonic bonds.

In at least one embodiment, the proximal section of each folded portion is directly attached to the elastomeric film layer by adhesive.

In at least one embodiment, the proximal section of each folded portion is directly attached to the elastomeric film layer by ultrasonic bonds.

In at least one embodiment, the at least one of the first and second nonwoven web layers further comprises at least one end portion that is substantially planar.

In at least one embodiment, the at least one end portion is ultrasonically bonded to at least one of the elastomeric film layer and the other one of the first and second nonwoven web layers.

In at least one embodiment, the elastic panel is a fastener of an absorbent article.

In at least one embodiment, the at least one of the first and second nonwoven web layers comprises at least one other group of folded portions, each folded portion comprising a first fold line and a second fold line so that the folded portion is divided into a proximal section, a distal section and a medial section disposed between the proximal and distal sections, the proximal section being directly attached to the other one of the first and second nonwoven web layers and the medial and distal sections not being directly attached to the other one of the first and second nonwoven web layers so that the folded portions extend to allow the web panel to stretch non-elastically.

According to an exemplary embodiment of the present invention, an absorbent article has an inside surface that faces a wearer's body when the absorbent article is worn, and an outside surface opposite the inside surface, and the absorbent article comprises: a liquid pervious topsheet; a backsheet, at least a portion of the backsheet being liquid impervious; a front waist portion comprising a first side front panel and a second side front panel; a back waist portion; a crotch portion longitudinally extending between the front waist portion and the back waist portion; an absorbent assembly disposed between the topsheet and the backsheet; and a first fastener disposed at the first side front panel and a second fastener disposed at the second side front panel for respective attachment to the back waist portion to fasten the absorbent article around the waist of the wearer, the first and second fasteners each comprising: an elastic panel comprising: a first nonwoven web layer; a second nonwoven web layer; and an elastomeric film layer disposed between the first and second nonwoven layers, at least one of the first and second nonwoven web layers comprising: at least one group of folded portions, each folded portion comprising a first fold line and a second fold line so that the folded portion is divided into a proximal section, a distal section and a medial section disposed between the proximal and distal sections, the proximal section being directly attached to the elastomeric film layer and the medial and distal sections not being directly attached to the elastomeric film layer so that the folded portions extend to allow the web panel to stretch elastically.

In at least one embodiment of the absorbent article, the first and second fasteners comprise fastening components.

In at least one embodiment of the absorbent article, the fastening components are hook or loop fastener components.

In at least one embodiment of the absorbent article, the at least one of the first and second nonwoven web layers comprises at least one other group of folded portions, each folded portion comprising a first fold line and a second fold line so that the folded portion is divided into a proximal section, a distal section and a medial section disposed between the proximal and distal sections, the proximal section being directly attached to the other one of the first and second nonwoven web layers and the medial and distal sections not being directly attached to the other one of the first and second nonwoven web layers so that the folded portions extend to allow the web panel to stretch non-elastically.

Other features and advantages of embodiments of the invention will become readily apparent from the following detailed description, the accompanying drawings and the appended claims.

BRIEF DESCRIPTION OF THE DRAWINGS

The features and advantages of exemplary embodiments of the present invention will be more fully understood with reference to the following, detailed description when taken in conjunction with the accompanying figures, wherein:

FIG. 3A is a planar view of an elastic laminate according to an exemplary embodiment of the present invention;

FIG. 3B is a cross-sectional view of the elastic laminate of FIG. 3A taken along line B-B;

FIGS. 7A-7C are cross sectional view showing a method of making an elastic laminate according to an exemplary embodiment of the present invention;

FIGS. 9A and 9B show construction of an absorbent article using an elastic laminate according to an exemplary embodiment of the present invention; and FIG. 10 shows construction of an absorbent article using an elastic laminate according to an exemplary embodiment of the present invention.

DETAILED DESCRIPTION

Figure 1A:
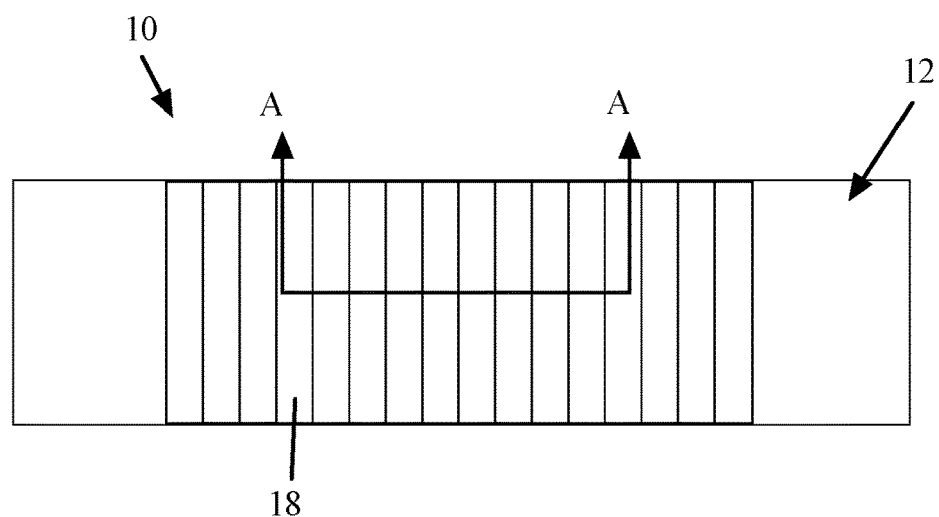
FIG. 1A is planar view of an elastic laminate according to an exemplary embodiment of the present invention.

The present invention is directed to an extensible web for use in an absorbent article. In an exemplary embodiment, the web is a laminate made up of one or more nonwoven layers each having portions bonded to an elastomeric film and portions that are not directly attached to the elastomeric film. Each unattached portion includes folds that allow the unattached portion to lay flat against an adjacent bonded portion. In an exemplary embodiment, the unattached portion is releasably bonded to the adjacent bonded portion. When the web is stretched upon placement of the article on the wearer, the folded portions at least partially unfold and lift off the adjacent bonded portions so that the nonwoven layers elongate with the elastomeric film. The extensible web may be formed with or without an elastomeric film, or may be formed with one or more zones in which an elastomeric film is present and one or more zones that are devoid of elastomeric film. In embodiments without elastomeric film and in embodiments including zones that are devoid of elastomeric film, when a cross-direction tension force is applied to the web, the folded portions unfold to allow the entire web or the portions of the web devoid of elastomeric film to extend in a substantially non-elastic manner. The inventive extensible web may be used to form at least part of a component of an absorbent article, such as, for example, a fastener ear or a waist portion.

The headings used herein are for organizational purposes only and are not meant to be used to limit the scope of the description or the claims. As used throughout this application, the words "may" and "can" are used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the figures.

In the discussion that follows, the term "body-facing surface" refers to a portion of a structure that is oriented towards a body surface, and the "garment-facing surface" refers to a portion of the structure that is oriented towards a garment and is typically opposing the body-facing surface and may be referred to as such. As used herein, the term "body surface" refers to a portion of an individual's body that the absorbent article is disposed with for collecting and absorbing fluid discharge from the individual. As used herein, the term "absorbent article," "absorbent garment" or "garment" refers to garments that absorb and contain exudates, and more specifically, refers to garments that are placed against or in proximity to the body of the wearer to absorb and contain the various exudates discharged from the body.

A non-exhaustive list of examples of absorbent garments includes diapers, diaper covers, disposable diapers, training pants, feminine hygiene products and adult incontinence products. The term garment includes all variations of absorbent garments, including disposable absorbent garments that are intended to be discarded or partially discarded after a single use (i.e., they are not intended to be laundered or otherwise restored or reused) and unitary disposable absorbent garments that have essentially a single structure (i.e., do not require separate manipulative parts such as a diaper cover and insert). As used herein, the term "diaper" refers to an absorbent garment generally worn by infants and incontinent persons about the lower torso.

Absorbent garments and diapers may have a number of different constructions. In each of these constructions it is generally the case that an absorbent core is disposed between a liquid pervious, body-facing topsheet, and a liquid impervious, exterior facing backsheet. In some cases, one or both of the topsheet and backsheet may be shaped to form a pant-like garment. In other cases, the topsheet, backsheet and absorbent core may be formed as a discrete assembly that is placed on a main chassis layer and the chassis layer is shaped to form a pant-like garment. The garment may be provided to the consumer in the fully assembled pant-like shape, or may be partially pant-like and require the consumer to take the final steps necessary to form the final pant-like shape, such as by fastening one or more fastener tabs.

In the case of some diapers and most adult incontinent products, the garment often is provided fully formed with factory-made side seams and the garment is donned by pulling it up the wearer's legs. In the case of most diapers, wherein, for example, a baby lies on his or her back, a caregiver usually places the diaper between the baby's legs, pulls the front end of the diaper up between the legs and then fastens one or more closure tabs from the back of the diaper to the front, thereby forming a pant-like structure. For clarity, the present invention is described herein only with reference to a diaper-type garment in which the topsheet, backsheet and absorbent core are assembled into a structure that forms a pant-like garment when secured on a wearer using fastening devices, although the invention may be used with any other type of absorbent garment that may benefit from the use or addition of fastener tabs.

Figure 1B:
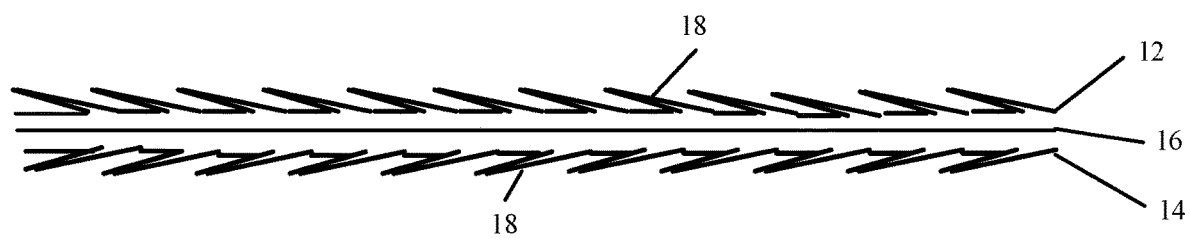
FIG. 1B is a cross-sectional view of the elastic laminate of FIG. 1A taken along line A-A.

FIGS. 1A and 1B illustrate an elastic web panel, generally designated by reference number 10, according to an exemplary embodiment of the present invention. FIG. 1A is a planar view of the panel 10 and FIG. 1B is a cross-sectional view of the panel 10 taken along line A-A in FIG. 1A. The panel 10 includes first and second nonwoven layers 12 and 14, and an elastomeric film layer 16 disposed between the nonwoven layers 12, 14. Each nonwoven layer 12, 14 includes folded portions 18.

Figure 2A:
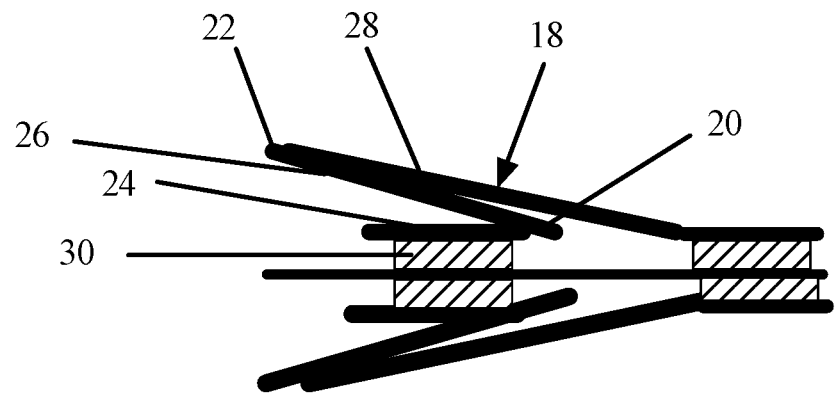
FIG. 2A is magnified cross-sectional view of a folded portion of a nonwoven web layer according to an exemplary embodiment of the present invention.
Figure 2B:
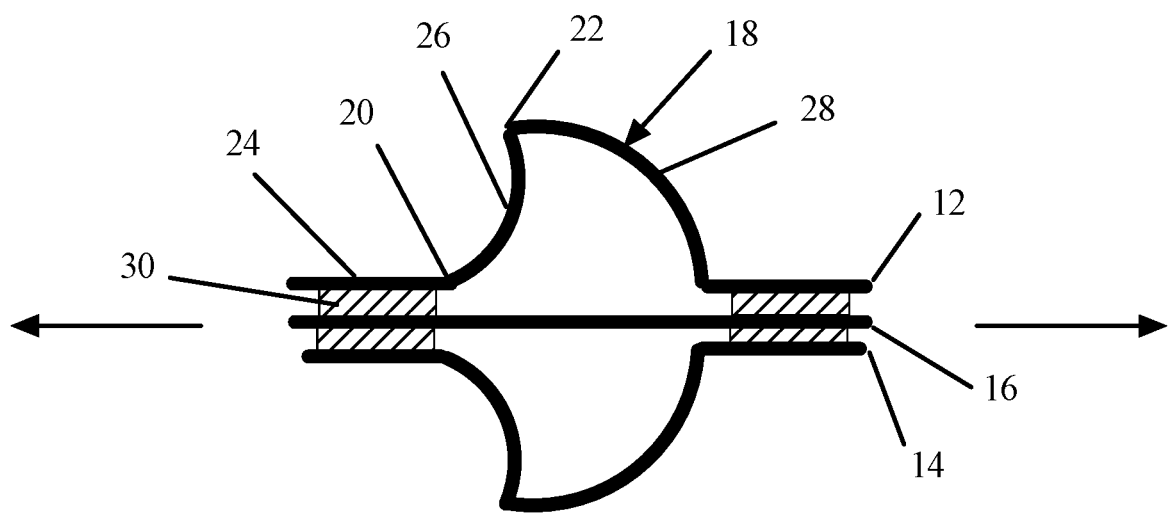
FIG. 2B is a magnified cross-sectional view of a folded portion of a nonwoven web layer according to an exemplary embodiment of the present invention as extended due to stretching of the laminate.

FIGS. 2A and 2B are a magnified cross-sectional views illustrating in more detail the folds in the nonwoven layers 12, 14. Each folded portion 18 is folded along a first fold line 20 and a second fold line 22 so that the folded portion 18 takes on a substantially z-shaped configuration. The first fold line 20 divides the folded portion 18 into a proximal section 24 (i.e., a section of the folded portion that is closest to the elastomeric film layer 16) and an intermediate section 26. The second fold line 22 divides the folded portion into the intermediate section 26 and a distal section 28 (i.e., a section of the folded portion 18 that is furthest from the elastomeric film layer 16).

In an exemplary embodiment, the proximal sections 24 of the folded portions 18 are directly attached to the elastomeric film layer 16, while the intermediate and distal sections 26, 28 are not directly attached to the elastomeric film layer 16. In this regard, hot melt adhesive 30 may be used to fix the proximal sections 24 to the elastomeric film layer 16. Further, the proximal, intermediate and distal sections 24, 26, 28 may be lightly bonded together using, for example, ultrasonic bonding so that the folded portions 24, 26, 28 lay substantially flat on top of one another prior to stretching of the elastic laminate 10. As shown in FIG. 2B, when a stretch force is applied to the elastic laminate 10, the light ultrasonic bonds begin to break, thereby allowing the folded portions 18 to unfold along fold lines 20, 22 and the nonwoven layers 12, 14 to elongate along with the elastomeric film layer 16.

FIGS. 3A and 3B illustrate an elastic web panel, generally designated by reference number 100, according to another exemplary embodiment of the present invention. FIG. 3A is planar view of the panel 100 and FIG. 3B is a cross-sectional view of the panel 100 taken along the line B-B in FIG. 3A. The panel 100 includes first and second nonwoven layers 112 and 114, and an elastomeric film layer 116 disposed between the nonwoven layers 112, 114. Each nonwoven layer 112, 114 includes first and second groups 130, 132 of folded portions 118. Each nonwoven layer 112, 114 also includes substantially planar medial non-folded portion 134 disposed between the first and second groups 130, 132 of folded portions 118 and substantially planar lateral non-folded portions 136, 138 extending outwards from the first and second groups 130, 132. As in the previous embodiment, each folded portion 118 is folded along fold lines so that the folded portion 118 takes on a substantially z-shaped configuration. Although each nonwoven layer 112, 114 includes two groups of folded portions 118 in the present embodiment, it should be appreciated that each nonwoven layer 112, 114 may include any number of such groups. As indicated by the sloped lines in FIG. 3B, in accordance with a preferred embodiment, the folded portions 118 within one group are folded in a direction opposite to that of the folded portions 118 of a laterally opposed group and in a same direction as that of the folded portions 118 of a vertically opposed group, although the folding is not limited to this configuration. The groups of folded portions 118 allow the user to extend the panel 100 a certain extent without having to necessarily stretch all groups of folded portions 118, thereby maintaining at least some of the substantially flattened shape of the panel 100. All groups of folded portions 118 may be unfolded to achieve the fully extended shape of the panel 100.

Figure 4A:
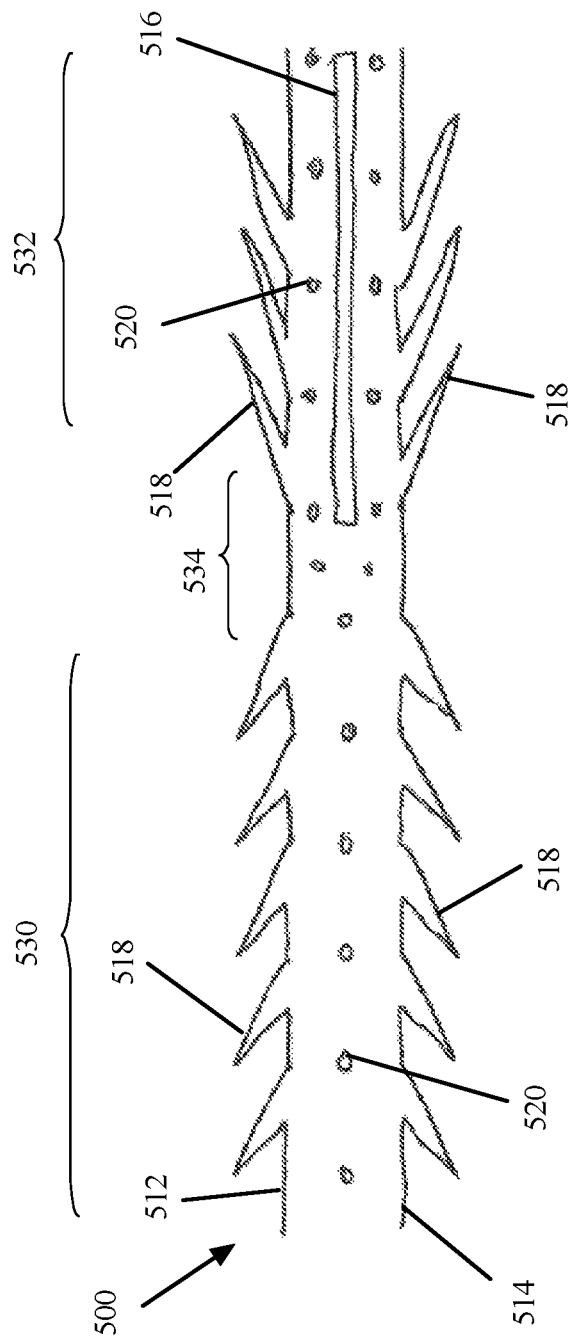
FIGS. 4A and 4B are cross-sectional view of a web panel according to an exemplary embodiment of the present invention showing extension of the web panel.
Figure 4B:
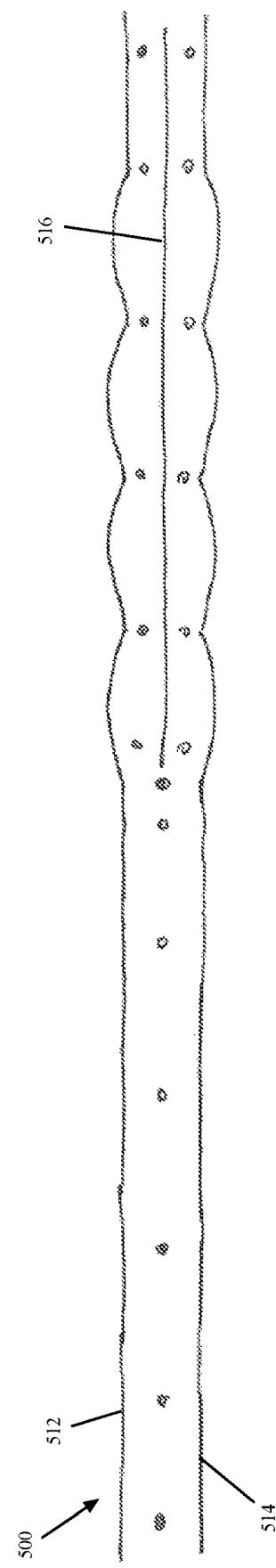

FIGS. 4A and 4B are cross-sectional views of web panel, generally designated by reference number 500, according to an exemplary embodiment of the present invention. The panel 500 includes first and second nonwoven layers 512 and 514, and an elastomeric film layer 516 disposed between the nonwoven layers 512, 514 along only a portion of the panel 500. Each nonwoven layer 512, 514 includes first and second groups 530, 532 of folded portions 518. The elastomeric film layer 516 in this embodiment extends only between the nonwoven layers 512, 514 within the second groupings 532 of folded portions 518. Each nonwoven layer 512, 514 also includes a substantially planar medial non-folded portion 534 disposed between the first and second groups 530, 532 of folded portions 518. As in the previous embodiment, each folded portion 518 is folded along fold lines so that the folded portion 518 takes on a substantially z-shaped configuration. Although each nonwoven layer 512, 514 includes two groups of folded portions 518 in the present embodiment, it should be appreciated that each nonwoven layer 512, 514 may include any number of such groups, with the elastomeric film layer 516 extending between one or more of the groups. It should be appreciated that the panel 500 may include more than one elastomeric film layer so that, for example, a separate elastomeric film layer may be present between corresponding groups of folded portions. Hot melt adhesive 520 is used to fix the proximal sections of the folded portions 518 within the groups 532 to the elastomeric film layer 516 and, within the groups 530, to the adjacent nonwoven layer 512, 514. As shown in FIG. 4A, the folded portions 518 within one group are folded in a direction opposite to that of folded portions 518 within a laterally opposed group.

As shown in FIG. 4B, when the panel 500 is subjected to tensile forces in the cross-direction, the folded portions 518 within groups 532 unfold to allow the panel 500 to stretch with recovery capabilities due to the presence of the elastomeric film layer 516, while the folded portions 518 within groups 530, 530 unfold to allow the panel 500 to extend without recovery. The panel 500 may be configured as a fastening panel for an absorbent article. Specifically, the panel 500 can be prepared and assembled to fit both as a custom fit for a waist dimension, as well as with a portion that includes an elastic engine, to produce a retracting force for a flexible and self-adjusting fit. The two regions of folds, one with and one without elastic properties can be prepared based on max elongation required dimensions, as well as percentile of elongation of an elastic engine.

Figure 5:
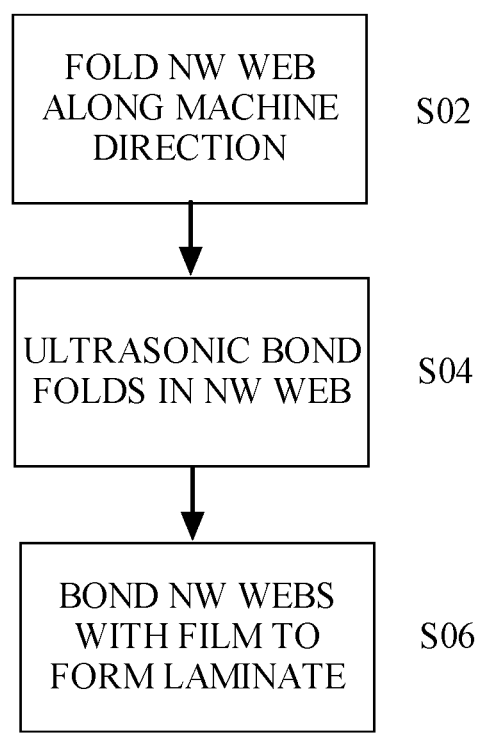
FIG. 5 is a flow chart of a method for making an elastic laminate according to an exemplary embodiment of the present invention.
Figure 6A:
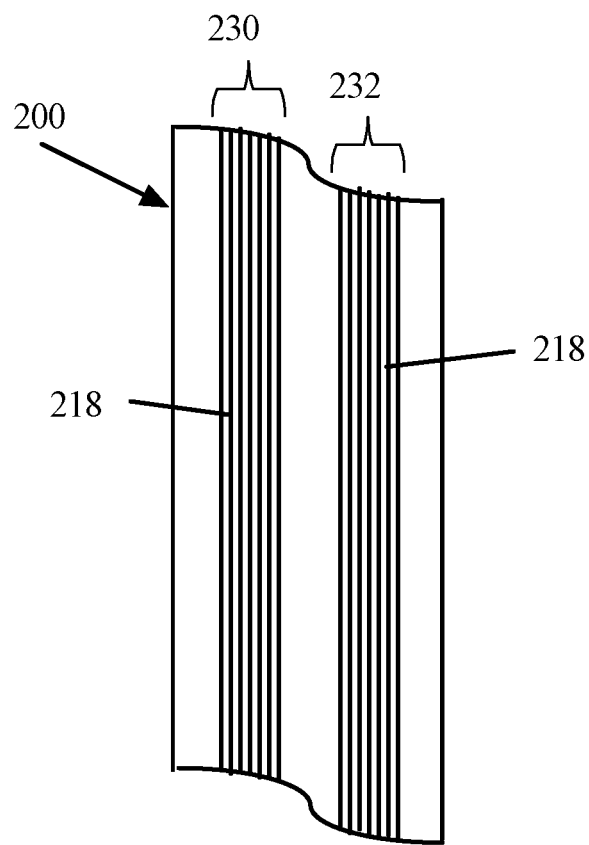
FIG. 6A is a partial planar view of a nonwoven web showing folds formed during a method of making an elastic laminate according to an exemplary embodiment of the present invention.

FIG. 5 is a flow chart of a method for forming an elastic laminate panel according to an exemplary embodiment of the present invention. In step S02 of the method, each nonwoven web intended for the panel is fed to a folding machine that forms at least one group of folded portions in the nonwoven web. The folds are formed so that the fold lines extend in the machine direction. FIG. 6A shows a nonwoven web 200 after step S02 with groups 230, 232 of folded portions 218 formed by folds extending in the machine direction.

Figure 6B:
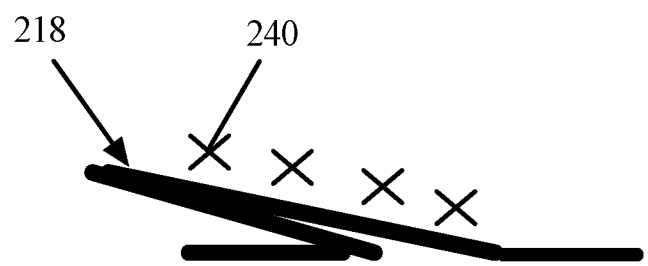
FIG. 6B is a cross sectional view of a folded portion of a nonwoven web showing ultrasonic bonds formed during a method of making an elastic laminate according to an exemplary embodiment of the present invention.

In step S04, each folded nonwoven web is fed to an ultrasonic bonding unit where ultrasonic bonds are formed in the nonwoven web. The ultrasonic bonding is intended to stabilize the folds in the nonwoven web so that the folds do not release during further processing. FIG. 6B shows one of the folded portions 218 after ultrasonic bonds 240 have been formed to lightly bond together the individual folds within the folded portion 218. The force of the bonds is based on converting speed, with the qualitative goal of stabilizing the folds for further processing, without damaging the nonwoven fibers. As an alternative to ultrasonic bonding, the folded nonwoven webs may be fed through a high pressure nip unit that stabilizes the folds and provides the nonwoven webs with a flat profile.

Figure 6C:
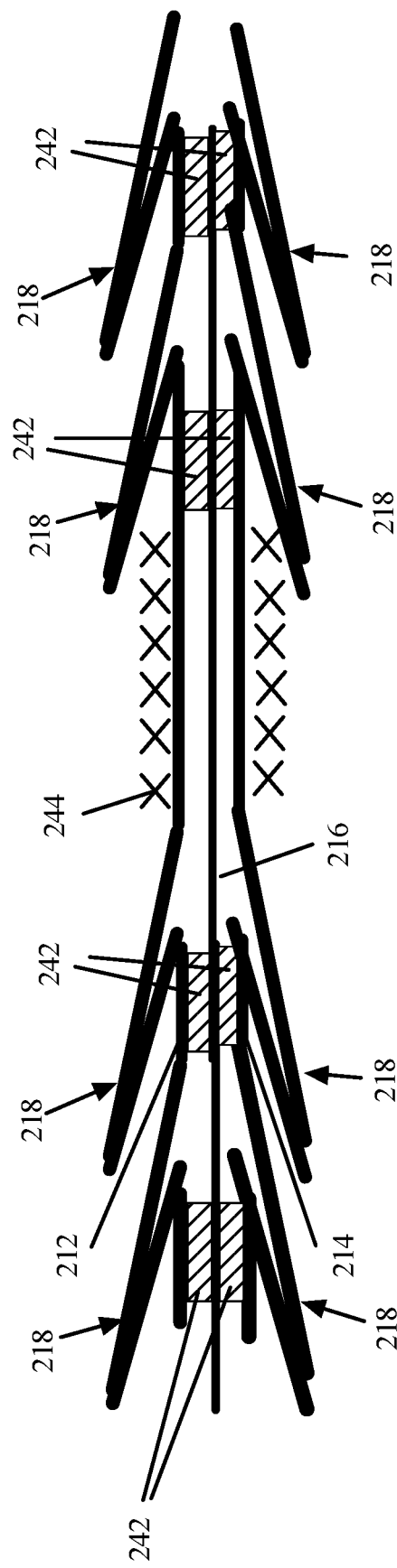
FIG. 6C is a cross sectional view of a laminate construction showing application of adhesive and ultrasonic bonds during a method of making an elastic laminate according to an exemplary embodiment of the present invention.

In step S06, the folded nonwoven webs and an elastomeric film are bonded together to form the laminate construction. In this regard, as shown in FIG. 6C, strips of hot melt adhesive 242 may be applied to the nonwoven webs 212, 214 so as to affix each nonwoven web to the elastomeric film 216. As described previously, the bonding of the nonwoven webs to the elastomeric film results in one section of each folded portion 218 being directly affixed to the elastomeric film 216, with the remaining sections not being directly affixed. Also, as shown in FIG. 6C, ultrasonic bonds 244 may be used to hold the laminate together at portions between the groups 230, 232 of folded portions 218 and at lateral unfolded portions. For example, referring back to the embodiment shown in FIGS. 3A and 3B, ultrasonic bonding may be used at medial non-folded portions 134 and at lateral non-folded portions 136, 138.

According to another exemplary embodiment, rather than bonding using hot melt adhesive, the entire laminate is bonded ultrasonically. In this regard, as shown in FIG. 7A, step S06 may include a first sub-step in which the nonwoven webs 212, 214 and the elastomeric film 216 are subjected to ultrasonic bonding at medial and lateral unfolded portions so as to form the laminate construction. As shown in FIG. 7B, in another sub-step, the laminate is subjected to tensioning in the cross direction to at least partially unfold the folded portions 218. Ultrasonic bonds are then applied to proximal sections of each folded portion 218 to affix the nonwoven webs 212, 214 to the elastomeric film 216 at those sections. As shown in FIG. 7C, in another sub-step, the cross direction force is released so that the laminate relaxes back to its original configuration, thereby allowing the folded portions 218 to return to a substantially flattened state and resulting in encapsulation of bond lanes under the folded portions 218. In order to further flatten the folded portions 218, the laminate panel may be fed to a flattening device where the laminate panel may be subjected to heat and/or pressure. In an exemplary embodiment, the flattening device includes driven coated rolls, set at a pre-determined angle, that assist the folds in the nonwoven webs 212, 214 to return to their original configuration. Subsequently, the web may be subjected to a mechanical pressure, such as a nip roll, to compact the web.

The nonwoven web layers used in the elastic laminate according to exemplary embodiments of the present invention may have a basis weight of 10 gsm to 25 gsm. The nonwoven web layers may have the same basis weight or different basis weights. The basis weights may be selected to provide the elastic laminate with desired extensibility and strength.

In an exemplary embodiment, the elastomeric film used in the elastic laminate has a basis weight of 10 gsm to 50 gsm. Suitable elastomeric films include, for example, ElastiPro®, available from Clopay Plastic Products Co., Inc., Mason, Ohio, USA and films available from Tredegar Film Product Corporation of North Chesterfield, Va., USA. The elastic laminate can also be prepared by extruding polymer such as Kraton G1643, available from Kraton Performance Polymers Inc., Houston, Tex., USA.

Figure 8:
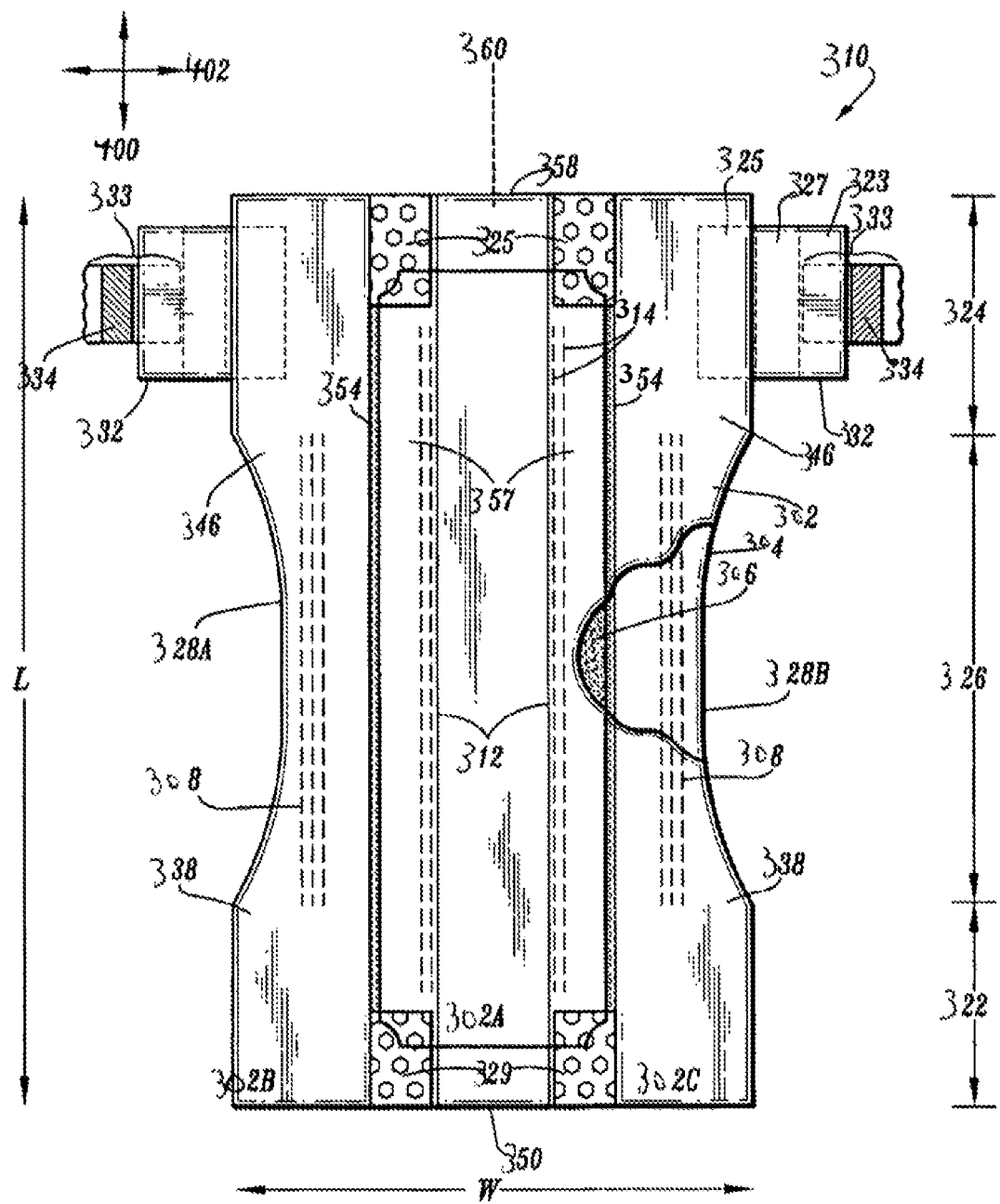
FIG. 8 is a planar view of an absorbent article according to an exemplary embodiment of the present invention.

FIG. 8 illustrates an absorbent article, generally designated by reference number 310, according to an exemplary embodiment of the present invention. It should be appreciated that application of the inventive elastomeric laminate panel is not limited to the general construction of the absorbent article shown in FIG. 8, and may be used in any other absorbent article configuration with appropriate variations in dimensions and materials.

FIG. 8 shows the diaper 310 in a relaxed condition with the effects of the elastics removed for purposes of clarity in the description. The diaper 310 chassis generally has an hourglass shape. The chassis generally can be defined in terms of a front waist region 322, a back waist region 324, and a crotch region 326. Those skilled in the art will recognize that "front" and "back" are relative terms, and these regions may be transposed without departing from the scope of the present invention. Alternatively, the diaper chassis can be configured in a generally rectangular shape or in a "T" shape. The diaper preferably comprises a topsheet 302, a backsheet 304, which may be either a different size than the topsheet 302 or may be substantially coterminous with the topsheet 302, and an absorbent core 306 disposed between at least a portion of the topsheet 302 and backsheet 304. Throughout this description, the terms "topsheet" and "backsheet" denote the relationship of these materials or layers with respect to the absorbent core 306. It is understood that additional layers may be present between or beyond the absorbent core 306 and the topsheet 302 and backsheet 304, and that additional layers and other materials may be present on the side opposite the absorbent core 306 from either the topsheet 302 or the backsheet 304. A pair of leg openings 328a, 328b extend along at least a portion of the crotch region 326 and one or more pairs of leg elastics 308 (three pairs are shown in FIG. 8) may be disposed to extend adjacent to leg openings 328a, 328b. Of course, in other embodiments, the number of leg elastics 308 may be increased, decreased or omitted altogether.

The diaper 310 generally has a longitudinal direction 400 that extends generally parallel to the front-to-back axis of a wearer, and a lateral direction 402 that extends generally parallel to the side-to-side axis of a wearer. The diaper 310 generally is symmetrical about a longitudinal centerline 360, but also may have asymmetrical components or shapes. The terms "inboard" or "proximal," and "outboard" or "distal," as used herein, refer to positions generally along the lateral direction 402, with "inboard" locations being located closer to the longitudinal centerline 360 than "outboard" locations. "Outward" and "inward" mean in an outboard or inboard direction, respectively.

The diaper 310 may further include a waste containment system in the form of waste containment flaps 312 (also known as inner leg gathers ("ILG's"), unitary leg gathers or standing leg gathers). Waste containment flaps 312 preferably extend from the front waist region 322 to the back waist region 324 along opposite sides of the longitudinal center line 360 of the diaper 310, or alternatively only along a portion thereof. The front waist region 322 and rear waist region 324 preferably include side panels, or ear portions 338, 346, extending outward from the leg openings 328a, 328b to provide the garment 310 with an hourglass shape.

The backsheet 304 may be made from any suitable pliable liquid-impervious material known in the art. Typical backsheet materials include films of polyethylene, polypropylene, polyester, nylon, and polyvinyl chloride and blends of these materials. For example, the backsheet can be comprised of a pigmented polyethylene film having a thickness in the range of 0.02-0.04 mm.

The backsheet 304 and the topsheet 302 preferably are "associated" with one another. The term "associated" encompasses configurations whereby the topsheet 302 is directly joined to the backsheet 304 by affixing the topsheet 302 directly to the backsheet 304, and configurations whereby the topsheet 302 is indirectly joined to the backsheet 304 by affixing the topsheet 302 to intermediate members which in turn are affixed to the backsheet 304. While the backsheet 304 and topsheet 302 in the preferred embodiment have substantially the same dimensions, they may also have different dimensions.

In addition, the backsheet 304 may be covered with a fibrous, non-woven fabric layer such as is disclosed, for example, in U.S. Pat. No. 4,646,362, which is incorporated herein by reference in its entirety. Materials for such a fibrous outer liner include a spun-bonded non-woven web of synthetic fibers such as polypropylene, polyethylene or polyester fibers; a non-woven web of cellulosic fibers, textile fibers such as rayon fibers, cotton and the like, or a blend of cellulosic and textile fibers; a spun-bonded non-woven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers.

The backsheet 304 may comprise multiple panels, such as three panels wherein a central poly backsheet panel is positioned adjacent the absorbent core while outboard non-woven breathable side backsheet panels are attached to the side edges of the central poly backsheet panel. The backsheet may also be formed from microporous poly coverstock for added breathability. In other embodiments, the backsheet may be a laminate of several sheets. The backsheet may further be treated to render it hydrophilic or hydrophobic, and may have one or more visual indicators associated with it, such as labels indicating the front or back of the diaper or other characters or colorations. The present invention is not limited to any particular backsheet material or construction.

The waste containment flaps 312 may be formed from separate elasticized strips of material that are associated with the topsheet, backsheet or both, or otherwise integrated into the garment. In another preferred embodiment, the topsheet 302 and backsheet 304 have similar dimensions or different dimensions, but in either case, the waste containment flaps 312 are attached to the topsheet 302 or to some intermediate element which in turn is attached to the topsheet 302. The waste containment flaps 312 may be treated with a suitable surfactant to modify their hydrophobicity/hydrophilicity or imbued with skin wellness products as desired. Each waste containment flap 312 preferably includes a portion that folds over onto itself to form an enclosure. One or more elastic members 314 may be secured in the enclosure in a stretched condition. Various other configurations of topsheets 302 and waste containment systems, such as flaps 312, are known in the art, and the present invention is not intended to be limited to any particular design for these components.

Each leg opening 328a, 328b may be provided with a leg elastic containment system 308, sometimes referred to as conventional leg gathers. In an illustrative embodiment, three strands of elastic threads are positioned to extend adjacent each leg openings 328a, 328b between the topsheet 302 and the backsheet 304. The selection of appropriate elastics and the construction of leg elastic containment systems are known in the art. For example, the leg elastics 308 may be ultrasonically bonded, heat/pressure sealed using a variety of bonding patterns, or glued to the diaper 310. Leg gathers 312 may be formed with or as separate members from topsheet 302.

Various commercially available materials may be used for the leg elastics 308 and elastic members 314, such as natural rubber, butyl rubber or other synthetic rubber, urethane, elastomeric materials such as spandex, which is marketed under various names, including LYCRA® (DuPont), GLOSPAN™ (Globe) and SYSTEM 7000™ (Fulflex), and so on. The present invention is not limited to any particular elastic material or to any particular shape, size or number of elastics.

The underlying structure beneath the topsheet 302 may include, depending on the absorbent garment construction, various combinations of elements, but in each embodiment, it is contemplated that the absorbent garment preferably will include an absorbent core 306. Although the absorbent core 306 depicted in FIG. 8 has a substantially rectangular shape as viewed in the plan view, other shapes may be used, such as a "T" shape or an hourglass shape. The absorbent core 306 may extend into either or both of the front and back waist regions 324, 322. The shape and construction of the absorbent core 306 may be selected to provide the greatest absorbency in target areas where body fluids are most likely to strike the diaper 310, which is often referred to as zoned absorbency. The absorbent core 306 may also comprise a number of layers of similar or different construction. The absorbent core may be associated with the topsheet 302, backsheet 304, or any other suitable part of the garment 310 by any method known in the art, in order to fix the absorbent core 306 in place.

Generally, in an illustrative embodiment, the absorbent core 306 comprises particles of superabsorbent material (SAP) distributed within a fibrous structure. Additional fibrous or particulate additives may be disposed within the absorbent core 306 to add to the core's strength and SAP efficiency or to otherwise enhance the performance of the garment. The absorbent core 306 may be partially or wholly surrounded by additional layers (not shown) added to provide further benefits. The additional layer or layers may comprise any useful layer known in the art or developed hereafter, such as a fluid acquisition layer, a distribution layer, an additional fibrous layer optionally containing superabsorbent particles (SAP), a wicking layer, a storage layer, or combinations and fragments of these layers. Such layers may be provided to assist with transferring fluids to the absorbent core 306, handling fluid surges, preventing rewet, containing absorbent material, improving core stability, or for other purposes.

The absorbent core 306 may be made from any absorbent material or materials, or combinations of such materials, known in the art or hereafter discovered. In one embodiment of the invention, the absorbent core 306 comprises wood fibers or other fibers such as chemical wood pulp, fibrous absorbent gelling material, or any other suitable liquid absorbing material, such as commercially available fluff pulp or fluffed bleached kraft softwood pulp or fibrous absorbent gelling material. In another embodiment of the invention, the absorbent core 306 comprises a combination of a porous fibrous web and superabsorbent particles. Absorbent cores are known in the art and exemplary cores are disclosed, for example, in U.S. Pat. No. 5,281,207 issued to Chmielewski et al., U.S. Pat. No. 4,610,678 issued to Weisman et. al., U.S. Pat. No. 5,137,537 issued to Herron et. al., U.S. Pat. No. 5,147,345 issued to Young et. al., and U.S. Pat. No. 6,068,620 issued to Chmielewski, all of which are incorporated herein by reference in their entirety, and in a manner consistent with the present invention.

Preferably, the absorbent core is thin in order to improve the comfort and appearance of a garment. The importance of thin, comfortable garments is disclosed, for example, in U.S. Pat. No. 5,098,423 to Pieniak et al., which is incorporated herein by reference in its entirety and in a manner consistent with the present invention.

Topsheet 302 may be made of any suitable relatively liquid-pervious material currently known in the art or later discovered that permits passage of a liquid therethrough. Examples of suitable top sheet materials include nonwoven, spun-bonded or carded webs of polypropylene, polyethelene, nylon, polyester and blends of these materials, or perforated, apertured or reticulated films, and the like. Nonwoven materials are exemplary because such materials readily allow the passage of liquids to the underlying acquisition layer, and therethrough to absorbent core 306. The top sheet 302 is preferably formed of a single ply of nonwoven material that may be made of thermally bonded, spunbonded fibers, spunbond-meltblown-spunbond or fibers that have been hydroentangled, having a basis weight of, for example, 10-30 grams per square meter and having appropriate strength and softness for use as a topsheet in an application which will be in contact with human skin. Topsheet 302 may be treated with surfactant, rendering it hydrophilic to facilitate the passage of moisture through topsheet 302 and into the interior of absorbent assembly. The present invention is not intended to be limited to any particular material for top sheet 302 and other top sheet materials will be readily apparent to those skilled in the art.

The topsheet 302 may be formed from one or more panels of material. In the embodiment shown in FIG. 8, the topsheet 302 is made up of one panel across the entire width of the diaper and preferably is formed from a liquid-pervious material. Topsheet 302 preferably extends from substantially the front waist region 322 to the back waist region 324 or a portion thereof, and includes a surfactant (at least along the core area) to aid in the passage of exudates to the core 306.

Diaper 310 is fastened onto a wearer by using one or more, and preferably two, fastener tabs or fasteners 332. Fasteners 332 preferably are affixed to the chassis of the diaper 310 to extend laterally outward (i.e., in the lateral direction 402) from a waist region 322, 324 of the garment. The fastener tabs 332 preferably are positioned to extend outward from the ear portions 346 of the rear waist region 324, but the fastener tabs 332 may also be attached to extend outward from the front waist region 322, or from both waist regions. The fastener tabs 332 may extend from one, but preferably both, lateral sides of the diaper 310. The fasteners 332 may be attached to any part of the diaper chassis, such as topsheet 302, backsheet 304, outer cover or other layer of the diaper. The fastener tabs 332 may also be attached to either side of the diaper's chassis, to multiple layers of the chassis, or may be sandwiched between the various sheets comprising the chassis of the diaper 310. For example, fastener 332 may be positioned between topsheet 302 and backsheet 304. In this case, one side of fastener 332 is attached to the inside of backsheet 304, and topsheet 302 is glued to the other side of fastener 332. Variations on the number, location, and attachment configuration of the fasteners 332 will be apparent to those skilled in the art based on the teachings herein, and all such variations are within the scope of the present invention.

Each of a pair of closure tabs 333 is attached along distal portion 323 of fastener 332 by adhesive bonding. It is contemplated herein that fasteners 332 and closure tabs 333 may be formed with materials that are elastic, non-elastic or a combination thereof and may be attached to the diaper 310 or each other by adhesive, ultrasonic, thermal bonding or the like. Closure tab 333 may include any hook-and-loop type material, adhesive, or other type of mechanical closure material 334 that is capable of holding diaper 310 on a wearer. Closure tab 333 operates by engaging with or adhering to a corresponding surface, landing zone or object (not shown) located on the opposite end of the diaper 310, preferably front waist region 322.

In the present exemplary embodiment, the fasteners 332 are elastic web panels, such as the elastic web panels 10, 100, 500 described herein. In this regard, the fasteners 332 may be made of an elastomeric film sandwiched between first and second nonwoven layers, with each nonwoven layer including one or more groups of folded portions. The folded portions allow the fasteners to stretch in conformance with the wearer's body with limited or no bunching of the nonwoven layers which would otherwise contribute to wearer discomfort.

Figure 9B:
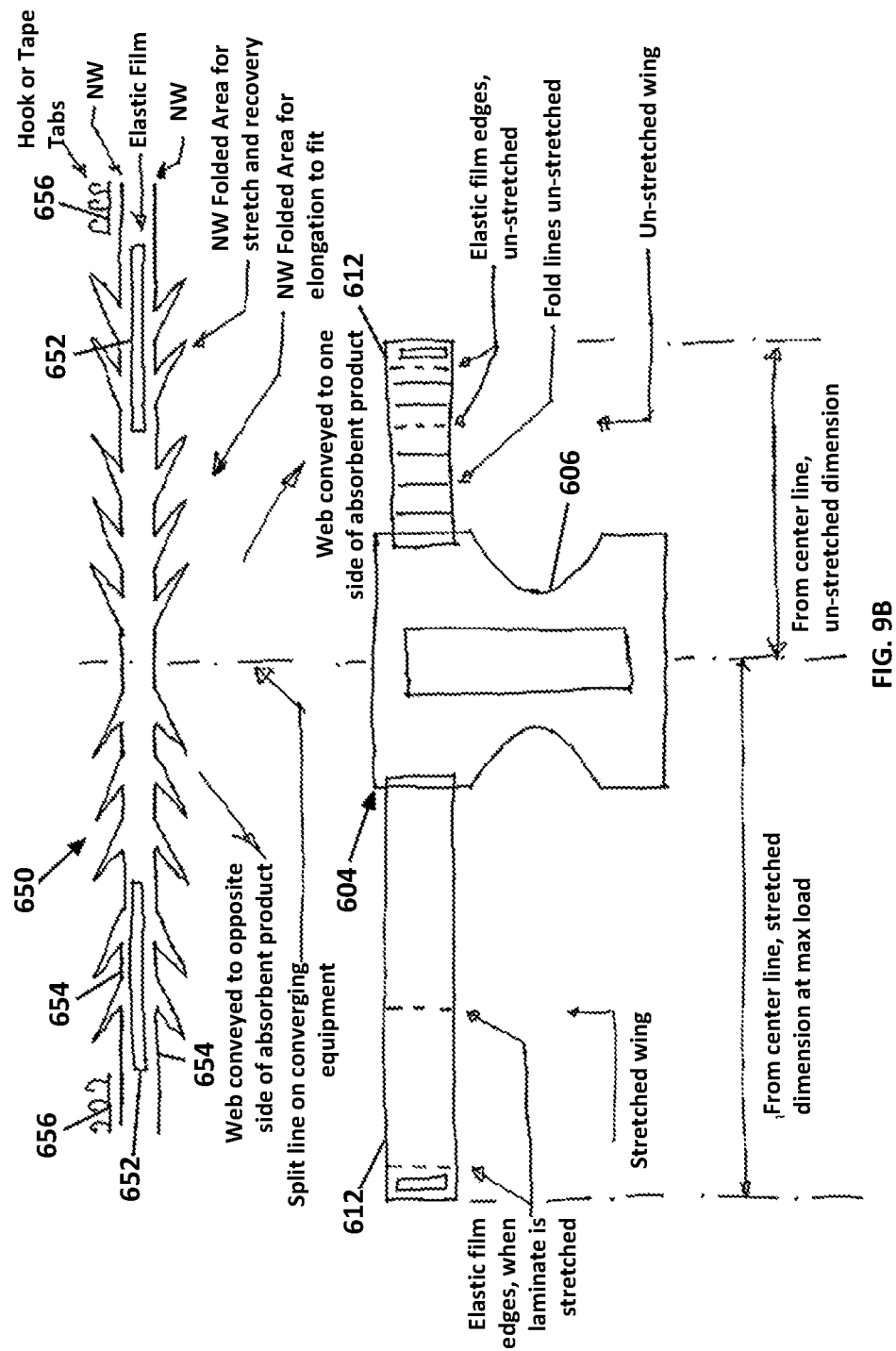

In exemplary embodiments, the configuration of the elastic web panels used for the diaper 310, including, for example, the number of groups of folded portions, the number of folds per group, the size of the folds, the presence or absence of elastomeric film in specific areas of the panel, and the materials used for the nonwoven layers and elastomeric film, may be adjusted for customization of the diaper 310. For example, the same chassis can be used for a variety of diapers with the parameters of the web panels being adjusted depending on desired fit of the diaper. In this regard, FIGS. 9A and 9B show the same diaper chassis 606 using two differently-configured web panels 610, 612 as fasteners so as to form two diapers 602, 604 with different fits. Specifically, the web panels 610 are formed from a web 650 that includes elastomeric film layers 652 disposed between nonwoven layers 654 that include at least one group of folded portions, as in the previously described embodiments. The elastomeric film layers 652 are laterally spaced apart at a middle portion of the web 650. Closure tabs 656 that include fastening material, such as hook or loop fastening material, are attached to the distal ends of the web 650. The web 650 is then separated at the middle portion to form the two web panels 610, and each web panel 610 is attached to a respective side of the chassis to form fasteners. As show in FIG. 9A, when the fastener is pulled outward away from the chassis 606, the unfolding of the folded portions in the web panel 610 allows the elastomeric layer to stretch, thereby elongating the fastener to allow for a secure fit around the waist of the wearer.

FIG. 9B is similar to the embodiment shown in FIG. 9A, except that the elastomeric film layers 652 do not extend between all groups of folded portions within the nonwoven layers 654. In the specific embodiment shown, only the groups of folded portions at the distal end portions of the web 650 are laminated with elastomeric film layers 652. Thus, when the web 650 is separated at the middle portion, the two web panels 612 are formed, each with a portion that is non-elastically extendable and another portion that is elastically extendible. As shown in FIG. 9B, when the fastener is pulled outward away from the chassis 606, the non-elastic portion of the fastener unfolds to accommodate a larger waist size, and the elastic portion of the fastener stretches to provide a secure fit.

According to another exemplary embodiment, web panels are releasably attached to the chassis for easy replacement with differently configured and/or sized web panels. For example, as shown in FIG. 10, a chassis 706 is configured for releasable attachment to corresponding fastener components 712 of separate web panels 708 (each web panel also includes another fastener 710 component as a closure tab for the absorbent article). The fastener components 712 may include either a hook or loop fastener for attachment of the web panels 708 to the chassis 706. In this regard, the web panels 708 may be placed on the back or front of the chassis 706. When the web panels 708 are placed on the chassis 706, the web panels 708 function as fasteners that hold the completed absorbent article construction around the wearer's waist. In this regard, the web panels 708 may be configured in accordance with any of the previously-described embodiments, including outer nonwoven layers each having one or more groups of folded portions, with or without an inner elastic film layer disposed between the nonwoven layers. In an exemplary embodiment, strips of panels are provided with perforated lines between each panel so that a single panel can be separated from the strip as needed and placed on a chassis. The strip may be provided in a roll, which in turn is placed in a dispenser, for ease in removing single panels from the roll. A number of rolls may be provided, with each roll including a different sized and/or differently configured panel. In use, a single-sized chassis may be used for all wearers, with adjustments in fit accomplished by using different sized panels as dispensed from a selected panel roll.

As discussed, the parameters of the web panel according to exemplary embodiment of the present invention may be tuned based on desired performance of the panel. For example, the strength at full elongation may be achieved solely by the material chosen for the application. The following examples illustrate this concept:

EXAMPLE 1

A three layer laminate panel was constructed, with both outer layers being made of 12 gsm spunbond nonwoven, and an inner elastic film layer.

EXAMPLE 2

A three layer laminate panel was constructed, with one outer layer being made of 18 gsm spunbond nonwoven, the other outer layer being made of 12 gsm spunbond nonwoven, and the same inner elastic film layer used in Example 1.

EXAMPLE 3

A three layer laminate panel was constructed, with one outer layer being made of 18 gsm spunbond nonwoven, the other outer layer being made of 18 gsm spunbond nonwoven, and the same inner elastic film layer used in Example 1.

EXAMPLE 4

A three layer laminate panel was constructed, with one outer layer being made of 22 gsm spunbond nonwoven, the other outer layer being made of 12 gsm spunbond nonwoven, and the same inner elastic film layer used in Example 1.

EXAMPLE 5

A three layer laminate panel was constructed, with one outer layer being made of 22 gsm spunbond nonwoven, the other outer layer being made of 18 gsm spunbond nonwoven, and the same inner elastic film layer used in Example 1.

EXAMPLE 6

A three layer laminate panel was constructed, with one outer layer being made of 22 gsm spunbond nonwoven, the other outer layer being made of 22 gsm spunbond nonwoven, and the same inner elastic film layer used in Example 1.

For each example, the tensile strength was tested using an Instron 3343 tensile tester, manufactured by Instron of Norwood, Mass., using Bluehill® 2 Software and the following test parameters: 500 N load cell, 3" wide sample, 3" clamping jaws. 12" per minute extension rate. The results are shown in Table 1.

TABLE 1

| EXAMPLE | TENSILE STRENGTH (grams max load) |
|---|---|
| 1 (12 gsm/12 gsm) | 4,740 |
| 2 (18 gsm/12 gsm) | 4,940 |
| 3 (18 gsm/18 gsm) | 5,450 |
| 4 (22 gsm/12 gsm) | 7,499 |
| 5 (22 gsm/18 gsm) | 7,487 |
| 6 (22 gsm/22 gsm) | 10,120 |

As another example, the elongation of the web panel may be controlled by the size and shape of the folds. Thus, to accomplish a laminated web, both for elongation properties alone and elongation with elastic retracting force, the following parameters can be configured as desired: 1) bond width and material used for nonwoven layers, for max load at elongation; 2) based on the desired elongation at full load (prior to break), the width of the web panel, prior to folding; and 3) based on the desired width of the web panel, the size and quantity of the folds in the web(s).

While particular embodiments of the invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method of forming an extendible web panel:
    forming at least one group of folded portions in at least one nonwoven web layer, each folded portion having a flattened, Z-configuration comprising a first fold line and a second fold line so that the folded portion is divided into a proximal section, a distal section and a medial section disposed between the proximal and distal sections; and
    attaching the at least one nonwoven web layer to an elastomeric film layer so that the proximal section of each folded portion is directly attached to the elastomeric film layer and the medial and distal sections of each folded portion are not directly attached to the elastomeric film layer and so that the folded portions extend to allow the web panel to stretch elastically.

2. The method of claim 1, wherein the at least one nonwoven web layer comprises a first nonwoven web layer and a second nonwoven web layer.

3. The method of claim 2, wherein at least one of the first and second nonwoven web layers comprises at least one end portion that is substantially planar.

4. The method of claim 3, further comprising the step of bonding the at least one end portion to at least one of the elastomeric film layer and the other one of the first and second nonwoven web layers.

5. The method of claim 2, further comprising:
    forming at least one other group of folded portions in at least one of the first and second nonwoven web layers, each folded portion of the at least one other group of folded portions comprising a first fold line and a second fold line so that the folded portion is divided into a proximal section, a distal section and a medial section disposed between the proximal and distal sections;
    attaching the at least one of the first and second nonwoven web layers to the other one of the first and second nonwoven web layers so that the proximal section of each folded portion of the at least one other group of folded portions is directly attached to the other one of the first and second nonwoven web layers and the medial and distal sections of the at least one other group of folded portions are not directly attached to the other one of the first and second nonwoven web layers and so that the folded portions of the at least one other group of folded portions extend to allow the web panel to stretch non-elastically.

6. The method of claim 1, wherein the at least one group of folded portions comprises a plurality of groups, and the at least one nonwoven web layer comprises generally planar sections between the plurality of groups.

7. The method of claim 1, further comprising the step of bonding together at least two of the proximal, medial and distal sections of the folded portions.

8. The method of claim 7, wherein the bonding comprises ultrasonic bonding.

9. The method of claim 1, wherein the proximal section of each folded portion is directly attached to the elastomeric film layer by adhesive.

10. The method of claim 1, wherein the proximal section of each folded portion is directly attached to the elastomeric film layer by ultrasonic bonds.

11. The method of claim 1, wherein the elastic panel is a fastener of an absorbent article.

* * * * *